US011257590B2

(12) United States Patent
Granneman (10) Patent No.: US 11,257,590 B2
(45) Date of Patent: Feb. 22, 2022

(54) METHOD AND APPARATUS FOR MEDICAL DEVICES UNDER REGULATORY CONTROL

(71) Applicant: KARL STORZ Imaging, Inc., Goleta, CA (US)

(72) Inventor: Russell Granneman, Goleta, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 916 days.

(21) Appl. No.: 15/448,385

(22) Filed: Mar. 2, 2017

(65) Prior Publication Data

US 2018/0253532 A1   Sep. 6, 2018

(51) Int. Cl.
*A61B 1/04* (2006.01)
*G16H 40/63* (2018.01)
*A61B 1/045* (2006.01)
*A61B 1/00* (2006.01)

(52) U.S. Cl.
CPC ......... *G16H 40/63* (2018.01); *A61B 1/00006* (2013.01); *A61B 1/00059* (2013.01); *A61B 1/043* (2013.01); *A61B 1/045* (2013.01)

(58) Field of Classification Search
CPC ...................................................... G16H 40/40
See application file for complete search history.

(56) References Cited

U.S. PATENT DOCUMENTS

| | | | | |
|---|---|---|---|---|
| 5,782,888 A * | 7/1998 | Sun | ...................... | A61B 5/0422 607/27 |
| 2002/0177751 A1 * | 11/2002 | Ueno | ................. | A61B 1/00009 600/160 |
| 2005/0054289 A1 * | 3/2005 | Salazar | ................. | H04W 92/02 455/39 |
| 2006/0094936 A1 * | 5/2006 | Russ | ..................... | H04M 1/725 600/300 |
| 2007/0027506 A1 * | 2/2007 | Stender | ................... | G06F 19/00 607/60 |
| 2009/0036943 A1 * | 2/2009 | Signoff | .................. | A61N 1/378 607/36 |
| 2009/0037634 A1 * | 2/2009 | Kuris | .................. | G06F 13/4081 710/303 |
| 2009/0150865 A1 * | 6/2009 | Young | ..................... | G06F 19/00 717/120 |
| 2009/0227839 A1 * | 9/2009 | Shimada | ............ | A61B 1/00055 600/118 |

(Continued)

*Primary Examiner* — Jefferey F Harold
*Assistant Examiner* — Timothy R Newlin
(74) *Attorney, Agent, or Firm* — Michael J. Loi; Nathan Calvert; David N. Villalpando (57) ABSTRACT

Systems, devices, methods, and program products are provided for operating a medical system that is operable within at least two different medical device regulatory classes. A device control module receives an indicator for performing at least one procedure with a medical device. Based on the indicator, it selects a binary image for booting the control module from among multiple images including a controlled-type and a non-controlled type, which operate in different regulatory classes. A controlled-type image, which may be FDA PMA or other regulatory classes, is verified to be unaltered, and is then used to operate as a regulated medical device. The indicator can be automatic or manual. The indicator may result from connection of a specific medical device or peripheral device, or may be user input.

8 Claims, 7 Drawing Sheets

(56) References Cited

U.S. PATENT DOCUMENTS

| | | | |
|---|---|---|---|
| 2010/0237709 A1* | 9/2010 | Hall .................. | B60L 11/182 |
| | | | 307/104 |
| 2015/0277986 A1* | 10/2015 | Zhang ................ | G06F 9/441 |
| | | | 713/2 |
| 2015/0339116 A1* | 11/2015 | Nekoomaram ........ | G06F 8/654 |
| | | | 717/169 |
| 2016/0378705 A1* | 12/2016 | Chung ................ | G06F 5/06 |
| | | | 710/14 |
| 2018/0247353 A1* | 8/2018 | Al-Ali ............... | G06Q 30/0601 |

\* cited by examiner

METHOD AND APPARATUS FOR MEDICAL DEVICES UNDER REGULATORY CONTROL

TECHNICAL FIELD OF THE INVENTION

The invention relates generally to the field of medical devices and more specifically to the field of medical device control software management.

BACKGROUND OF THE INVENTION

Various medical procedures require electronic systems (e.g., software and firmware (e.g., FPGA code) that are regulated by the FDA or other regulatory bodies and must be strictly controlled. For example, endoscopic fluorescence imaging systems capable of autofluorescence and/or Photodynamic Diagnosis (PDD) procedures are currently classified as an FDA Class III medical device, which is governed by a Premarket Approval (PMA) release and approval process.

Because of the risk profile of Class III devices, Class III devices are "locked down" such that no changes to system hardware, programmable hardware such as field-programmable-gate-array (FPGA) devices, or software are allowed without further FDA approval. This may take the form of a PMA supplement and can take six to twelve months to obtain. It may also require clinical testing for approval pending the level of change.

The typical approach to controlling and maintaining Class III and similarly PMA-controlled devices is to establish a unique part number for each device, which is only allowed to connect to an approved control module and other approved peripheral devices. Unfortunately, this process forces customers to purchase a separate, completely PMA-controlled set of equipment to perform procedures that involve a Class III device, even though the equipment is often suitable for use with other devices that are not controlled. This results in duplicated expenses in order to comply with regulations.

What is needed are improved ways to manage and control medical equipment to ensure the configuration reliably complies with regulations. What is further needed are ways to reduce cost by reducing unnecessary duplication of equipment.

SUMMARY OF THE INVENTION

It is an object of the invention to provide improvements to manage and control medical equipment to ensure the configuration reliably complies with regulations. It is a further object to reduce cost by reducing unnecessary duplication of equipment. It is a further object to help automate system setup for medical procedures to avoid errors and misuse of medical devices.

Systems, devices, methods, and program products are provided for operating a medical system that is operable within at least two different medical device regulatory classes. A device control module receives an indicator for performing at least one procedure with a medical device. The indicator can be automatic or manual. The indicator may result from connection of a specific medical device and/or peripheral device, or user input.

Based on the indicator, it selects a binary image for booting the control module from among multiple images, including a controlled-type and a non-controlled type. The different types are respectively capable of operating a medical device that is classified in a regulatory class that differs from the other.

For example, a controlled-type image, which may fall under FDA Class III/PMA or similar regulatory classes, is verified to be unaltered, and is then used to operate as a regulated (e.g., FDA Class III) medical device, whereas the non-controlled type is used to operate, for example, an FDA Class I and/or Class II device.

According to a first aspect of the invention, a method of operating a medical system that is operable within at least two different medical device regulatory classes is provided. The at least two different regulatory classes including a first regulatory class which is more tightly controlled or restricted by regulations, and a second regulatory class, which typically includes less tightly restricted. The method includes receiving an indicator for performing at least one medical procedure that utilizes a medical device. Then, based on the indicator, the method selects one of multiple binary images including data for booting a medical device control module, the multiple binary images including at least a controlled type binary image for operating as a first regulatory class medical device and a non-controlled type binary image for operating as a second regulatory class medical device. If the selected binary image is the controlled type binary image, the method boots the medical device control module from or otherwise operates the medical device control module via the controlled type binary image, and thereby operating (or otherwise providing) the medical device control module as the first regulatory class medical device for performing the at least one medical procedure.

In a first implementation of the first aspect, the first regulatory class medical device is of a class that requires FDA premarket approval and a second regulatory class medical device is of a class that does not require FDA premarket approval. For example, the first regulatory class medical device may be an FDA Class III medical device and the second regulatory class medical device may be one of an FDA Class I and Class II device.

In a second implementation of the above aspect and/or implementation, the medical device connected to the control module is a front end module for coupling an imaging scope to the medical device control module.

Receiving the indictor may include recognizing that the medical device has been coupled to the medical device control module and obtaining a device identifier for the medical device.

In a third implementation of the above aspect and/or implementations, the method further includes recognizing that a peripheral device has been coupled to the medical device control module, then obtaining a device identifier for the peripheral device. Then selecting one of multiple binary images is further based on the peripheral device identifier. The peripheral device may be a display module.

In a forth implementation of the above aspect and/or implementations, the medical procedure includes an endoscopic fluorescence imaging (EFI) procedure. Said EFI procedure may include at least one of a photodynamic diagnosis procedure and an autofluorescence procedure.

In a fifth implementation of the above aspect and/or implementations, the medical device is a fluorescence imaging scope or a combination of a fluorescence imaging scope and a front end module for coupling the fluorescence imaging scope to the medical device control module.

In a sixth implementation of the above aspect and/or implementations, the method further includes installing an update for a selected one of the multiple binary images being the non-controlled type.

In a seventh implementation of the above aspect and/or implementations, the method further includes, if the selected binary image is a non-controlled type binary image, booting the medical device control module from the non-controlled binary image and thereby operating the medical device control module as the second regulatory class medical device for performing the at least one medical procedure.

In an eighth implementation of the above aspect and/or implementations, the multiple binary images include program code for a microprocessor and FPGA configuration code for configuring at least one FPGA in the medical device control module.

According to a second aspect of the invention, a medical device control module is provided, either integrated with a medical device or configured to connect to a medical device. Alternatively, two or more medical control modules may operate cooperatively as the medical device control module. The control module is operable within at least two different medical device regulatory classes, the at least two different regulatory classes. The control module includes at least one digital processor and associated RAM memory, and non-transitory memory. The non-transitory memory holds at least one binary image of a controlled type for operating as a device within the first regulatory class, at least one binary image of a non-controlled type for operating as a device within the second regulatory class, and boot manager program code executable by the digital processor to perform the following: receive an indicator for performing at least one medical procedure that utilizes a medical device; based on the indicator, select one of the binary images for booting the medical device control module; determine if the selected binary image is a controlled type image, and if so, perform a verification of the image and then boot the medical device control module from the controlled type binary image. The at least one digital processor is operable to, after booting from the controlled type binary image, execute program code from the controlled type binary image for operating the medical device control module, and controlling the medical device, as a first regulatory class medical device for performing the at least one medical procedure.

In a first implementation of the second aspect, the boot manager program code further includes program code executable by the at least one digital processor for (i) recognizing that a medical device has been coupled to a medical device control module; (ii) obtaining a device identifier for the medical device. Selecting one of multiple binary images is, in this case, further based on the peripheral device identifier.

In a second implementation of the second aspect and/or above implementation, the boot manager program code further includes code executable by the at least one digital processor for recognizing that a peripheral device has been coupled to the medical device control module and obtaining a device identifier for the peripheral device, and then selecting one of multiple binary images is further based on the peripheral device identifier. The peripheral device may be a display module, for example.

In a third implementation of the second aspect and/or above implementations, the medical device connected to the control modules is a front end module for coupling an imaging scope to the control module. In some implementations, the medical device is configured to conduct EFI procedures (e.g., at least one of a PDD or AF procedure).

In a fourth implementation of the second aspect and/or above implementations, the first regulatory class medical device is of a class that requires FDA premarket approval and a second regulatory class medical device is of a class that does not require FDA premarket approval.

In a fifth implementation of the second aspect and/or above implementations, the medical device is a fluorescence imaging scope or a combination of a fluorescence imaging scope and a front end module for coupling the fluorescence imaging scope to the medical device control module.

In a sixth implementation of the second aspect and/or above implementations, the multiple binary images include program code for a microprocessor and FPGA configuration code for configuring at least one FPGA in the medical device control module.

In a seventh implementation of the second aspect and/or above implementations, the program code also includes update program code executable by the at least one digital processor to update a selected non-controlled binary image, and subsequently to recognize that a different medical device has been coupled to a medical device control module, obtain a device identifier for the different medical device, and based on the device identifier, select the updated binary image and then boot the medical device control module from the updated binary image.

In an eighth implementation of the second aspect and/or above implementations, the program code also includes controlled-update program code executable by the at least one digital processor to verify a replacement controlled binary image, remove a selected controlled binary image, and replace it with the replacement controlled binary image and subsequently to recognize that a different medical device has been coupled to a medical device control module, obtain a device identifier for the different medical device, and based on the device identifier, select the updated binary image and then boot the medical device control module from the updated binary image.

According to a third aspect of the invention, one or more tangible, non-transitory computer readable media, such as hard drives, SSD drives, or other data storage devices, are provided including program code such as that described with respect to the second aspect and implementations thereof. Implementations of the first aspect of the invention are also implementable according to the third aspect of the invention.

According to a fourth aspect, the functionality described herein for the implementations of the first aspect may be embodied as a medical system including the medical device control module and the medical device. Such a system may also include a front end module configured to connect the medical device to the control module. In some cases, the front end module is configured to provide a device identifier or a procedure identifier to the control module to assist the module in selecting an appropriate binary image.

According to a fifth aspect, a method of operating a medical system that is operable within at least two different medical device regulatory classes is provided. The at least two different regulatory classes including a first regulatory class and a second regulatory class. The method includes receiving an indicator for performing at least one medical procedure that utilizes a medical device. Based on the indicator, the method selects one of multiple binary images for operating a medical device control module. The multiple binary images including at least a controlled type binary image for a first regulatory class medical device and a non-controlled type binary image for a second regulatory class medical device.

If the selected binary image is the controlled type binary image, the method exclusively operates the medical device control module via the controlled type binary image and thereby providing the medical device control module as a part of the first regulatory class medical device for performing the at least one medical procedure. As used herein, "exclusively operates" means that the selected binary image operates the module at the exclusion of other possible binary images residing in said module or another module. This meaning does not exclude, for example, other functions based on user input, connected-device(s) input and the like that may control or otherwise influence aspects of the medical device control module during exclusive operation via the controlled type binary image.

Implementations of the first, second, third, and fourth aspects of the invention are also implementable according to the fifth aspect of the invention. For example, exclusively operating the medical device control module via a binary image may include booting said module from said binary image.

Implementations of the invention may also be embodied as software or firmware, stored in a suitable medium, and executable to perform various versions of the methods herein. These and other features of the invention will be apparent from the following description of the preferred embodiments, considered along with the accompanying drawings.

DETAILED DESCRIPTION OF EXAMPLE EMBODIMENTS

The present invention provides systems, methods, and control modules for managing the behavior of medical devices to comply with regulatory requirements across multiple (medical device) regulatory classes. The features herein provide, inter alia, the ability to recognize a configuration in which a regulatory control scheme or class applies and select an appropriate controlled binary image for booting, verify the image, and boot one or more designated modules accordingly. Preferred embodiments involve using a control module with various imaging scopes and peripheral devices.

Figure 1:
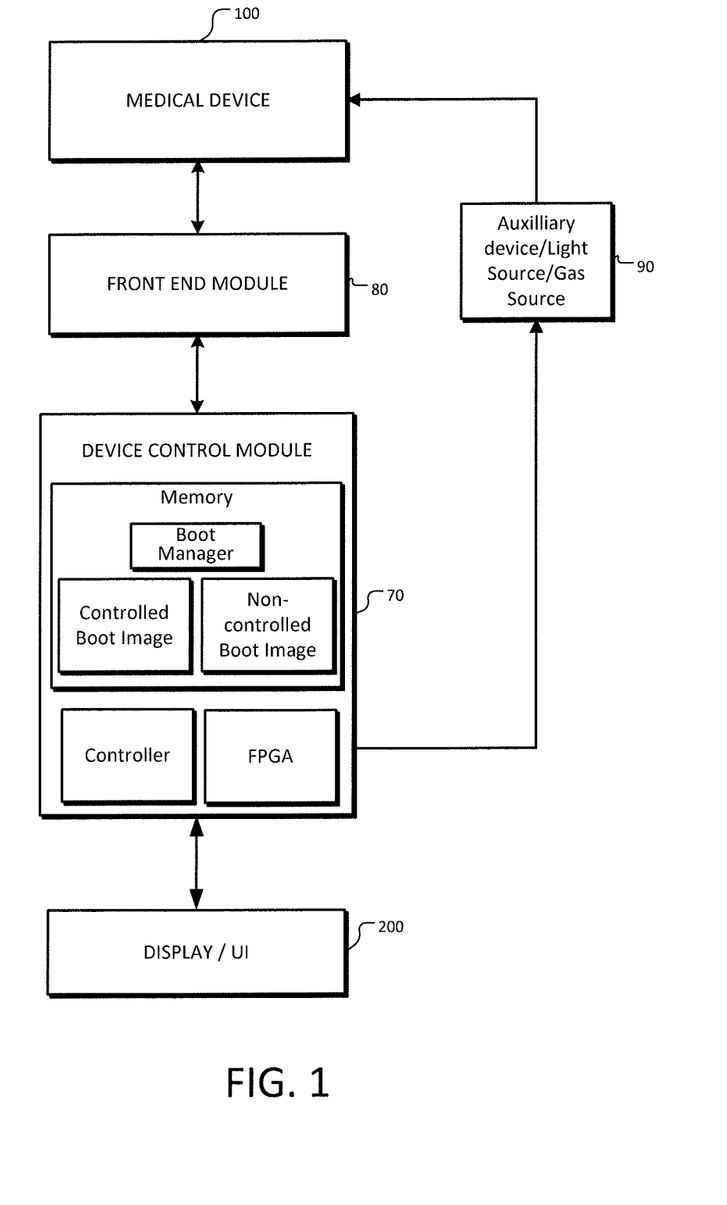
FIG. 1 is a block diagram of an example system of connected medical devices.

FIG. 1 is a system block diagram of a medical device control system according to an example embodiment. A medical device 100, preferably an imaging scope such as an endoscope, is communicatively coupled to a front end module 80, which couples to the device control module 70. Front end module 80 is an electronic module for communicating with a particular medical device 100, as will be further described below. Some embodiments may employ the configuration of FIG. 2A, in which no front end module is used, and instead the digital communications protocols and processing performed by module 80 are instead performed by the device 100 and device control module 70. Device control module 70 is preferably a camera control module (CCM), but may be a different type of medical device control module, such as a special purpose device for interfacing with suitable medical devices, or a computer programmed and configured for interfacing with such devices.

Also communicatively coupled to device control module 70 may be one or more auxiliary devices 90 such as a light source, insufflator, or other auxiliary device associated with the specific medical procedure that is desired. Generally device control module 70 may be programmed to receive an indicator that a particular medical procedure or procedure type is to be performed and/or a particular medical device will be utilized (e.g., a Class III device). As further described below, the indicator may include user input or may be determined automatically, or a combination of these two in which a user is provided choices based on the system configuration to select a desired procedure or procedure type.

The module may identify the connected devices and control the boot process for module 70 based on the configuration detected. For example, module 70 may identify auxiliary devices 90 (light sources, link modules, camera heads, displays etc.) that are also connected and determine if these devices is/are a PMA-controlled class of devices individually or in combination. If so, the device control module 70 may determine that the user wishes to boot from the PMA-locked or controlled binary image, which is bitwise identical to the FDA approved configuration.

As shown, the example design for device control module 70 includes at least one digital processor and associated RAM memory. The processor may be a microcontroller or a DSP, or a controller working together with an FPGA, which is preferably in a system-on-chip configuration with the controller. As shown, the module 70 also includes nontransitory computer memory containing at least two binary boot images, including at least one binary image of a controlled type and at least one binary image of a non-controlled type.

Each of these images typically includes all the program files needed to operate the control module to perform the desired functions for each respective hardware configuration. The device control module 70 also includes boot manager program code executable by the digital processor as further described below for controlling the boot process by selecting the correct boot image for the current hardware configuration, for recognizing that a medical device has been coupled to a medical device control module, such as the device connections in FIG. 1 and FIG. 2A.

Also connected to device control module 70 may be an electronic display device 200, which may be any suitable display for showing data or images obtained during the procedure, and also for presenting a user interface (UI) for the device control module. The display may be a touchscreen display, and other UI devices such as a mouse, joystick, or keyboard may be connected to module 70 as well.

Typically the depicted connections between devices are made with a cable that carries at least digital data connections, and may also carry other signals or electrical connections such as power supply voltages. However, this is not limiting and other versions may include wireless data and control connections accomplished typically with short range wireless pairing of devices by any suitably secure and reliable wireless connection standard.

Figure 2A:
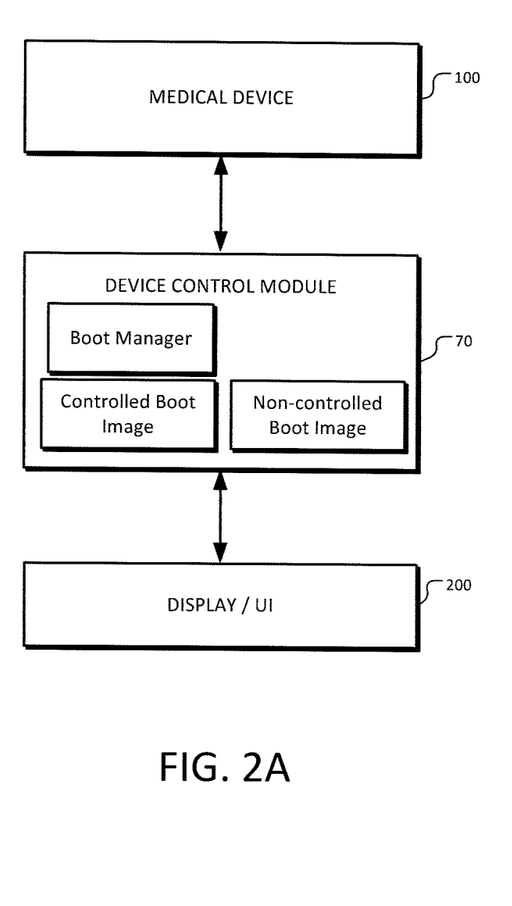
FIG. 2A is a block diagram of an alternative example system of connected medical devices.
Figure 2B:
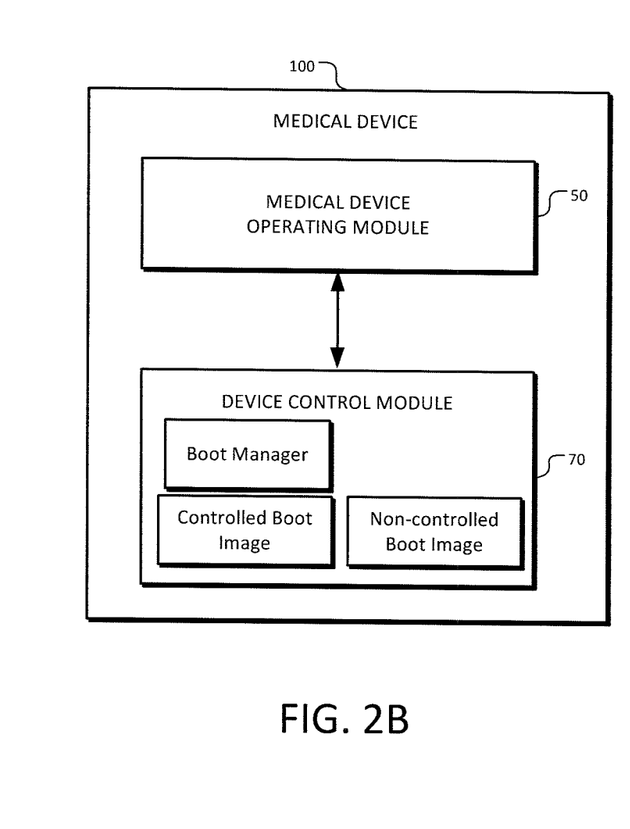
FIG. 2B is a block diagram of an example integrated medical device and control module.

FIG. 2B is a block diagram of an example embodiment including an integrated medical device 100 and including a device control module 70 and an operating module 50. Some of the techniques herein may be employed on such integrated devices, in which a boot manager controls the booting of the device from a controlled image or non-controlled image, as further described below.

Figure 2C:
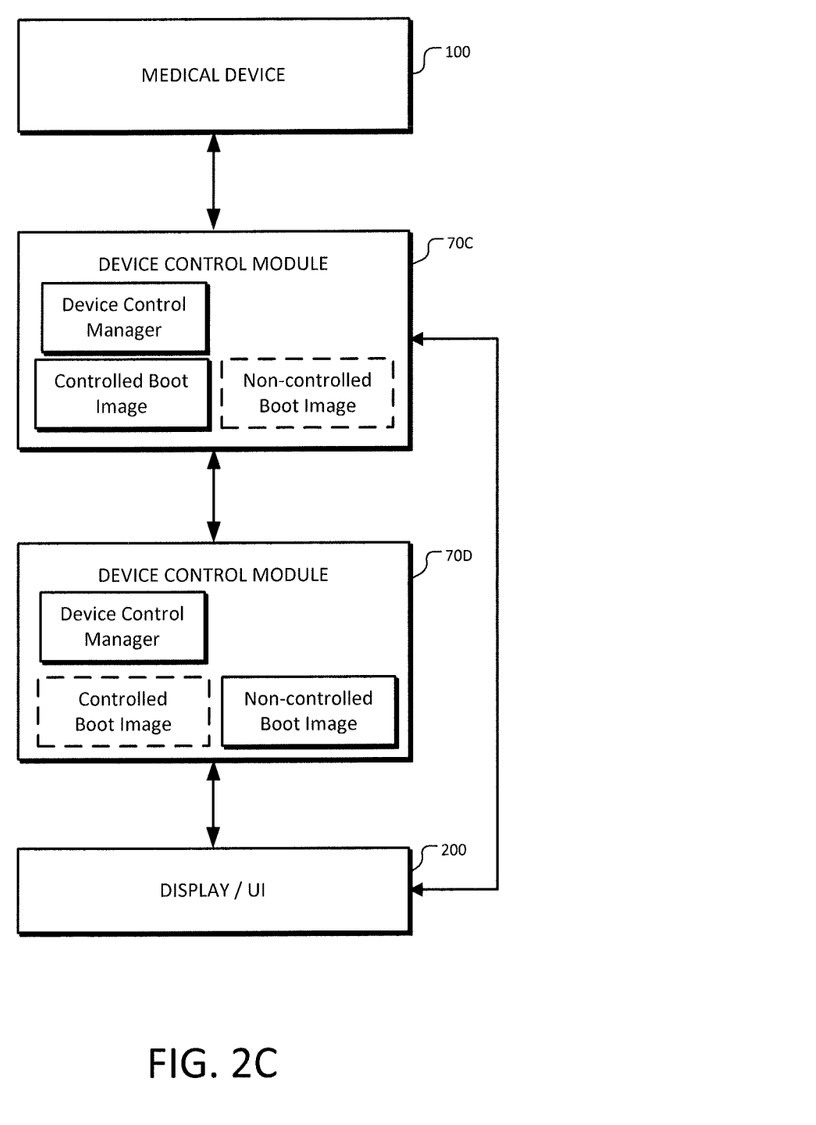
FIG. 2C is a block diagram of another example system embodiment.

FIG. 2C is a block diagram of an example embodiment including a medical device 100, an upstream device control module 70C, a downstream device control module 70D, and electronic display 200. Some of the techniques herein may be employed on such a system, in which a boot manager controls the booting of the device from a controlled image or non-controlled image, as further described below. Further still, embodiments according to FIG. 2C allow for switching between or among medical device classes without necessarily requiring a boot sequence, as further described below. Device control modules 70C and 70D each include a device control manager, which is similar to the boot manager and may include program code for providing the functionality described herein for the boot manager, and includes program code for recognizing that multiple control modules are connected in the system and managing communications between the devices as further described below. In the depicted configuration, upstream device control module 70C is communicatively coupled to medical device 100, and to downstream device control module 70D. Upstream device control module 70C may also be communicatively coupled directly to display/UI device 200, or may rely solely on relayed communications through downstream device control module 70D. Device control modules 70C and 70D may each include in memory multiple boot images, but configurations with multiple device control modules do not require that each include multiple boot images, as depicted by the dotted blocks in the diagram showing boot images that are optionally present.

Figure 3:
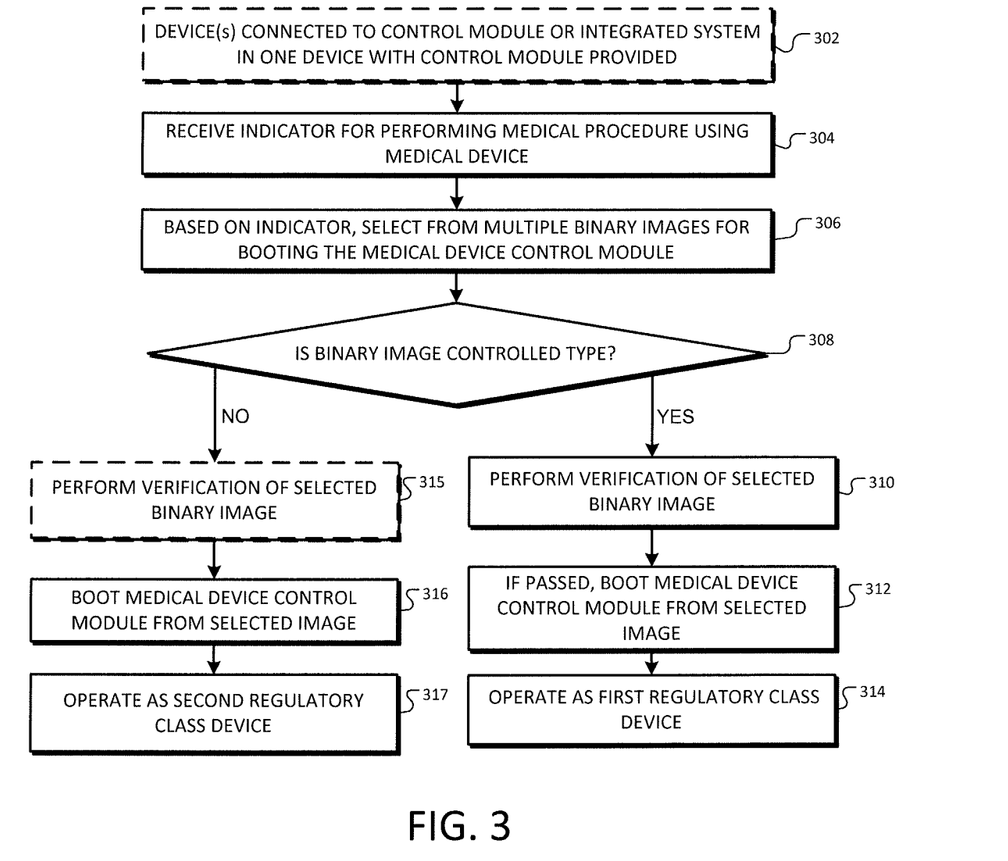
FIG. 3 is a flowchart of a process for managing a device control module according to some embodiments.

FIG. 3 is a flowchart of a process for managing a device control module according to some embodiments. The process is typically conducted by boot manager program code installed in the device control module 70 non-transitory memory (see, for example, FIGS. 1, 2A, and 2C).

Generally, the depicted process provides a method of operating a medical system that is operable within at least two different medical device regulatory classes, the at least two different regulatory classes including a first regulatory class and a second regulatory class, and controls the boot-up process to operate as a device in a particular regulatory class.

The process may begin at process block 302 with a medical device and possibly peripheral devices connected to a control module, such as in the example configurations of FIG. 1 and FIG. 2A, but it may also be conducted with an integrated system in a single medical device such as the example configuration of FIG. 2B.

In some other versions, one or more connected devices may be connected after the booting steps are performed rather than before. The connection may be a parallel cable, serial cable, or wireless direct connection or other suitable coupling such as a wireless network or wired network connection.

Next at block 304, the process receives an indicator for performing at least one medical procedure that utilizes a medical device. This indicator can have any suitable form for reliably controlling the boot-up process to operate the system. In some versions, the indicator is a user selection made from a number of available choices, such as from a prompt or interface on which a surgeon selects a medical procedure, which may include procedures that utilize a device under a PMA-regulatory scheme (e.g., an FDA Class III medical device).

In other versions, receiving the indicator may be conducted automatically by the control module 70 by, for example, checking for one or more connected devices, recognizing them, and interpreting them as an indicator accordingly (e.g., certain individual or specific combinations of connected devices may be an FDA Class III device).

In some versions, receiving the indicator further includes recognizing that a medical device or peripheral device is coupled to the device control module, such as by using any suitable signal from the coupled device: an analog high/low voltage value from the medical device (when connected to the medical device control module), a device identifier such as a model number, or a medical procedure identifier, which may identify a procedure that necessitates a Class III (or regulatory class equivalent) device. The indicator could also be a software message response from a connected device. The indicator may also be a combination of signals or messages from more than one connected device.

Next, at block 306, the process goes on to, based on the indicator, select one of multiple binary images for booting a medical device control module 70. The multiple binary images including at least a controlled type binary image for operating as a first regulatory class medical device and a non-controlled type binary image for operating as a second regulatory class medical device.

The phrase "binary image" describes binary data such as a file or group of files used to configure (e.g., boot or initialize) the control module 70, and is not used in the sense of a picture image. An example of said binary data includes files used to configure an FGPA and/or software aspects of control module 70.

The binary images may be "boot images" (images of a data drive from which a device is booted), however this is not limiting, and the binary images referenced herein may be images of drives, or may be other kinds of data such as other types of binary files or groups of files, if such data can be used to boot, initialize, or otherwise configure the medical device control module to a desired controlled configuration.

The binary images contain binary data for booting the control module 70, which may include software and/or hardware configuration data such as one or more of an operating system, executable programs, hardware programming data such as FPGA configuration data, and may contain data restricting operation of the control module or connected devices to selected modes or configurations. For example, a binary image for conducting a particular diagnostic procedure under regulatory control may contain configuration data restricting a connected endoscope to using only a particular combination of incident light and fluorescent light. As another example, a binary image may contain configuration data restricting a connected display module to a designated set of display settings for color display.

As discussed further below, a controlled type binary image is used for procedures governed by a regulatory or professional process to limit the device to be booted only by the specified image or with the specified configuration in the image. A non-controlled type may also be selected, which is typically allowed to have updates and other features upgraded after release without the strict regulatory review (e.g., PMA) of the controlled type image.

If the selected binary image is the controlled type binary image at block 308, the process goes to block 310 where it performs a verification of the image to confirm it as the data approved by the regulatory or professional approval process and may further verify the integrity of the image. Preferably this verification is done by calculating a checksum or other digital signature process on the image, and comparing the result to a validated checksum or digital signature maintained by the boot manager or by an outside server.

If the image passes verification, the process at block 312 proceeds to boots or otherwise initializes the medical device control module 70 from the controlled type binary image. This block may involve simply booting the control module 70 with the image, which then controls any connected medical devices 100 or medical device operating module 50 (FIG. 2B) according to the verified and approved programming provided in the image. Block 312 may also include sending specific initialization commands to a medical device 100 or medical device operating module 50 to initialize that device or module to the desired operating state.

Next at block 314, the process operating the medical device control module 70 as the first regulatory class medical device for performing the at least one medical procedure. The operation at block 314 may include any suitable first regulatory class medical procedure such as EFI. For example, it may be a photodynamic diagnosis procedure or autofluorescence procedure.

In the United States, the first regulatory class medical device may of a class that requires FDA premarket approval and a second regulatory class medical device is of a class that does not require FDA premarket approval. For example, the first regulatory class medical device may be an FDA Class III medical device and the second regulatory class medical device is one of an FDA Class I and Class II device. In many other countries, similar regulatory schemes are provided by regulatory bodies or international standards organizations, and the functionality provided by the binary images is adjusted correspondingly.

For example, the Medical Devices Bureau of Health Canada recognizes four classes of medical devices based on the level of control necessary to assure the safety and effectiveness of the device. Class I devices present the lowest potential risk and do not require a license. Class II devices require the manufacturer's declaration of device safety and effectiveness, whereas Class III and IV devices present a greater potential risk and are subject to in-depth scrutiny.

These classes of classes of medical devices correspond to the European Council Directive 93/42/EEC (MDD) devices: Class IV (Canada) generally corresponds to Class III (ECD); Class III (Canada) generally corresponds to Class IIb (ECD); Class II (Canada) generally corresponds to Class IIa (ECD); and Class I (Canada) generally corresponds to Class I (ECD).

Examples, under the Canadian regulatory scheme, include surgical instruments (Class I), contact lenses and ultrasound scanners (Class II), orthopedic implants and hemodialysis machines (Class III), and cardiac pacemakers (Class IV).

If the image is a non-controlled type binary image, the process at block 308 goes to block 315, where it may conduct a verification of the image, but this optional step would not typically conduct a verification against an image controlled by a regulatory process, and instead is for verifying the integrity of a non-controlled image that may be updated without regulatory approval.

At block 315, the process boots the medical device control module from the selected non-controlled image, and then at block 317 operates the system as a second regulatory class device to perform a medical procedure. It is noted that "operating the medical device control module as the first regulatory class medical device" includes a change of the mode or functioning of the medical device control module.

In some cases, as described below, a particular connected medical device or peripheral device may be required to operate the system as a first regulatory class medical device, however this not limiting and in many cases the same hardware present in the system may be operated within both regulatory classes. The method may also include installing an update for a selected one of the multiple binary images being the non-controlled type.

As discussed, a system employing the method may include an integrated device with a device control module 70 and the medical device constructed together, or a medical device control module 70 coupled to a medical device 100. In some versions, the medical device connected or logically coupled to the control module 70 may be a front end module 80 (FIG. 1), for coupling an imaging scope to the medical device control module 70. In some versions, the medical device is a fluorescence imaging scope or a combination of a fluorescence imaging scope and a front end module for coupling the fluorescence imaging scope to the medical device control module.

The method may further include recognizing that a peripheral device such as a display has been coupled to the medical device control module, and obtaining a device identifier for the peripheral device. In such case, selecting one of multiple binary images may be further based on the peripheral device identifier.

Figure 4:
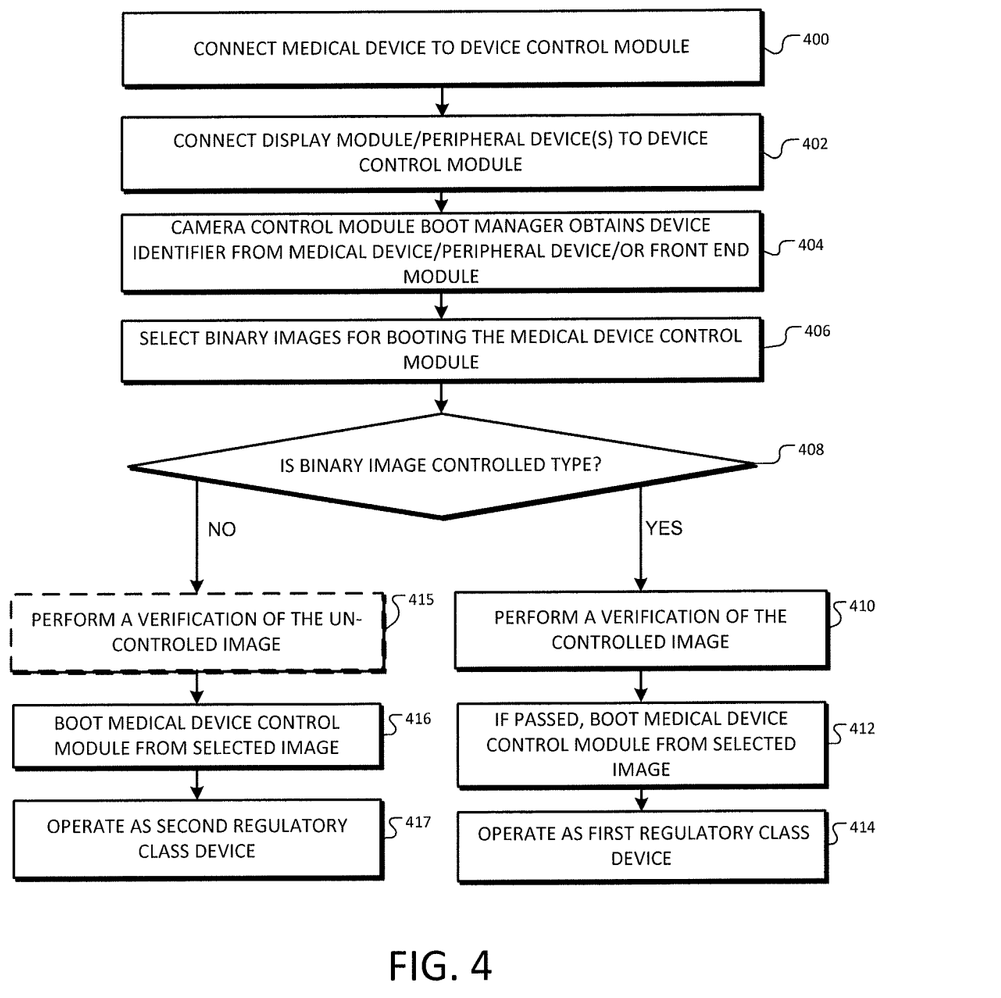
FIG. 4 is a flowchart of a process according to other example embodiments.

FIG. 4 is a flowchart of a process for operating a medical system according to another example embodiment. Generally, the automated portions of the process are conducted by a controller for a device control module such as those described above. At block 400, the process begins with connecting a medical device to a device control module. This typically occurs with a medical technician or surgeon physically connecting the devices or activating a wireless connection pairing the devices. The connection may be direct or through a front end module as described above with regard to FIG. 1.

Next at block 402, one or more display modules 200 or other peripheral devices 90 such as a light source are connected. At block 404, the boot manager program code runs to obtaining a device identifier for the connected medical device 100 or the front end module 80. The process at block 404 may also obtain device identifiers for one or more auxiliary devices 90 that may be connected or reconnected and based on the device identifier. Together these identifiers may be understood as a form of the indicator received at block 304 in the more generalized process of FIG. 3.

The boot manager program module may be already running waiting for a connection to be detected, or may check for connections when the device control module 70 is powered on or reset. Next, the process includes selecting one of the binary images for booting the medical device control module at block 406. The selection is preferably made based on any one of the device identifiers obtained, or based on recognizing a certain combination of device identifiers that is associated with a desired medical procedure having a desired boot image for operating the desired medical procedure.

For example, in one embodiment, the process includes determining which boot image to load depending on connected peripherals' diagnostic capabilities, recognized by looking up capabilities associated with the connected devices, for example in a local database or data table.

If a diagnostic capability such as EFI is indicated, the process may select the controlled boot image, which is capable of operating the system to perform the indicated diagnostic capability (and thus configures the system as a Class III device). Typically, the different boot images contain differently configured versions of the same operating system.

Next at block 408, the process checks if the selected binary image is a controlled type image, which may be done as part of selecting the image at block 406. When used in the U.S. market, for example, the system allows control of a Class III device, which would not be available to a non-controlled binary. The non-controlled binary can be updated with improved behaviors and changes as needed without the rigorous PMA supplement process.

If the selected boot image is controlled, the process at block 410 performs a verification of the image, which proceeds similarly to the steps of FIG. 3, as do the following steps which are not repeated here. If there were a required controlled type binary change, it can be submitted under an appropriate regulatory process such as the PMA supplement in the U.S., and once approved, rolled out for updating the controlled type binary along with updated verification information. Also, similarly to FIG. 3, block 415 may optionally perform a verification check on a non-controlled binary image if a non-controlled image is selected, and the operation proceeds to operate the system as a medical device of the second regulatory class.

Figure 5:
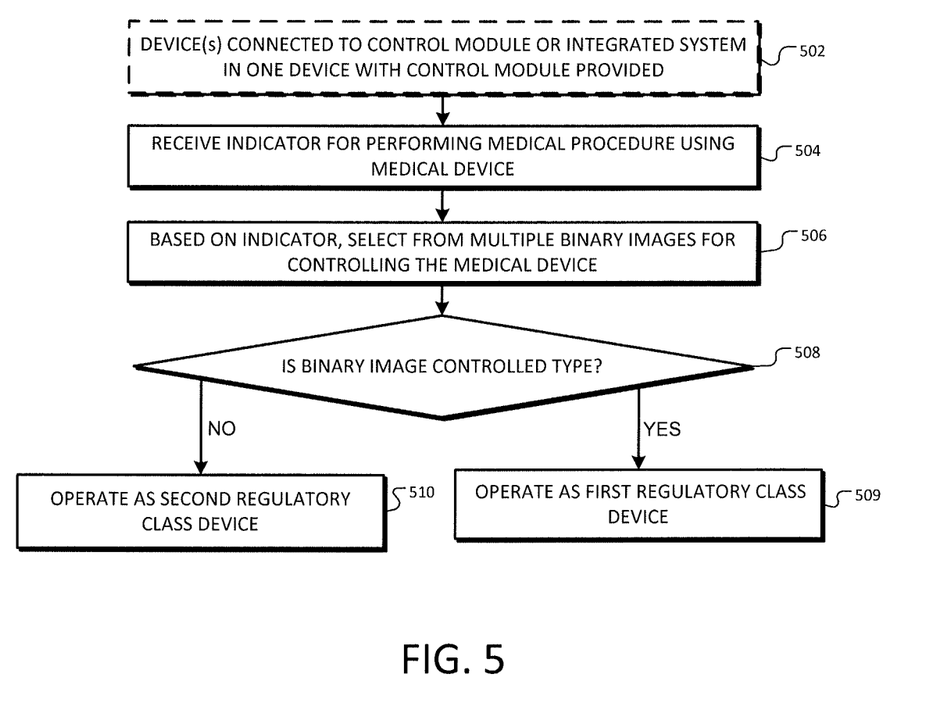
FIG. 5 is a flowchart of a process for operating a medical system according to another example embodiment.

FIG. 5 is a flowchart of a process for operating a medical system according to another example embodiment. The process may begin at process block 502 with a medical device and possibly peripheral devices connected to a control module, such as in the example configurations of FIG. 2C. The one or more connected devices may be connected after a booting step is performed.

Next at block 504, the process receives an indicator for performing at least one medical procedure that utilizes a medical device, as described above.

Next, at block 506, the process goes on to, based on the indicator, select one of multiple binary images for controlling/operating the medical device. The multiple binary images including at least a controlled type binary image for operating as a first regulatory class medical device and a non-controlled type binary image for operating as a second regulatory class medical device, wherein each image type may respectively reside in separate camera control modules, as shown in FIG. 2C.

In such cases, device control module 70C may simply pass a signal through to device control module 70D or conduct processing before sending the processing signal to device control module 70D and thereby effectively operating as a Class I or II device even if booted from a controlled binary. However, as a Class III device, device control module 70C would solely process medical device's 100 signals and send the signal to display 200 (i.e., a separate signal chain).

Such embodiments allow for toggling control of medical device 100 between device control module 70C and 70D without necessarily requiring a boot sequence when changing from a Class II/I device to a Class III device and vise-versa. Rather, control is "passed" between or among device control modules.

Next at block 508, if the indicator requires a controlled binary image, the process goes to block 509 where it operates the medical device control module 70 as the first regulatory class medical device for performing the at least one medical procedure.

If, at block 508, the image is a non-controlled type binary image, the process at block 508 goes to block 510, which operates the system as a second regulatory class device to perform a medical procedure. In some implementations, the process may allow a return to block 504 to receive a different indicator after operation in blocks 509 or 510. For example, if the process is employed with the system configuration of FIG. 2C, a first indicator may be received at block 504 directing the process to one of blocks 509 or 510 for performing a medical procedure, and then a second indicator may be received, directing the process to the other of blocks 509 or 510, where a second medical procedure may be performed. In such case, the control of medical device 100 is passed or toggled between device control module 70C and device control module 70D.

Program code for achieving such a handover of control and directing communications between the various devices may reside in the device control manager of 70C, the device control manager of 70D, or the display/UI device 200. For example, the device control manager of downstream device control module 70D may include program code for recognizing that module 70D has been coupled to module 70C, and for presenting an interface at display/UI device 200 for inputting the indicators. The downstream device control manager of module 70D may then direct communications from upstream device control module 70C accordingly, either processing data for operation according to the non-controlled boot image activated on downstream control module 70D, or causing data to be passed from upstream device control module 70C to display/UI device 200 for operation according to the controlled boot image activated on upstream device control module 70C.

Figure 6:
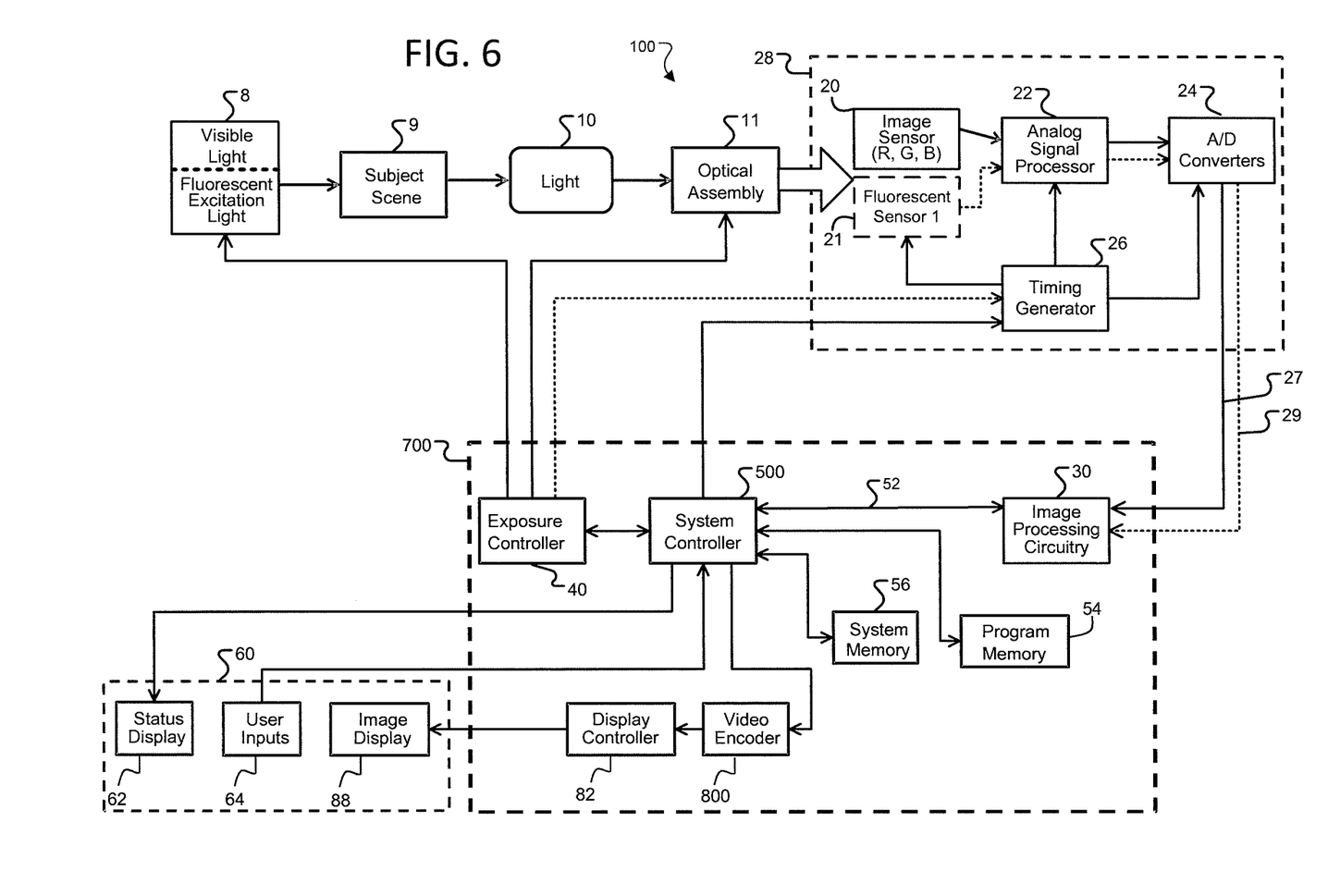
FIG. 6 is a hardware block diagram of an example image capture device according to an example embodiment of the invention.

Referring to FIG. 6, a system block diagram including an image capture device according to an example embodiment of the invention is shown. The depicted fluorescent image capture device 100 is an example implementation of medical device 100 as described herein.

A light source 8 illuminates subject scene 9 with visible light and/or fluorescent excitation light, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser LEDs positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is focused to form an image at a solid-state image sensor(s) 20 and/or fluoresced light sensor(s) 21.

Optical assembly 11 includes at least one lens, which may be a wide-angle lens element such that optical assembly 11 focuses light which represents a wide field of view. Image sensor 20 (which may include separate R, G, and B sensor arrays) and fluoresced light sensor 21 convert the incident visible and invisible light to an electrical signal by integrating charge for each picture element (pixel). It is noted that fluoresced light sensor 21 is shown as an optional dotted box because embodiments may use the RGB image sensor 20 to detect only white light images or to also detect fluoresced light (e.g., NIR ICG FI). The latter scheme may be used when the fluoresced light is in a spectrum detectable by light sensor 20 that is in or near the visible light spectrum typically detected by a RGB sensor arrays.

The image sensor 20 and fluoresced light sensor 21 may be active pixel complementary metal oxide semiconductor sensor (CMOS APS) or a charge-coupled device (CCD).

The total amount of light 10 reaching the image sensor 20 and/or fluoresced light sensor 21 is regulated by the light source 8 intensity, the optical assembly 11 aperture, and the time for which the image sensor 20 and fluoresced light sensor 21 integrates charge. An exposure controller 40 responds to the amount of light available in the scene given the intensity and spatial distribution of digitized signals corresponding to the intensity and spatial distribution of the light focused on image sensor 20 and fluoresced light sensor 21.

Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller may also control the optical assembly 11 aperture, and indirectly, the time for which the image sensor 20 and fluoresced light sensor 21 integrate charge. The control connection from exposure controller 40 to timing generator 26 is shown as a dotted line because the control is typically indirect.

Typically exposure controller 40 has a different timing and exposure scheme for each of sensors 20 and 21. Due to the different types of sensed data, the exposure controller 40 may control the integration time of the sensors 20 and 21 by integrating sensor 20 up to the maximum allowed within a fixed 60 Hz or 50 Hz frame rate (standard frame rates for USA versus European video, respectively), while the fluoresced light sensor 21 may be controlled to vary its integration time from a small fraction of sensor 20 frame time to many multiples of sensor 20 frame time. The frame rate of sensor 20 will typically govern the synchronization process such that images frames based on sensor 21 are repeated or interpolated to synchronize in time with the 50 or 60 fps rate of sensor 20.

Analog signals from the image sensor 20 and fluoresced light sensor 21 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 20 also functions to detect the fluoresced light, fluoresced light data is included in the image signal 27, typically in one or more of the three color channels.

Image processing circuitry 30 includes circuitry performing digital image processing functions. Timing generator 26 produces various clocking signals to select rows and pixels and synchronizes the operation of image sensor 20, analog signal processor 22, and A/D converter 24. Image sensor assembly 28 includes the image sensor 20, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 500 controls the overall operation of the image capture device based on a software program stored in program memory 54. Program memory 54 may include one or multiple memory devices, and will typically store the boot manager or device control manager program code as described above, as well as the required boot images. This memory can also be used to store user setting selections and other data to be preserved when the camera is turned off.

System controller 500 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 800 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60 is an example implementation of a display/UI device 200 as described herein, including all or any combination of image display 88, user inputs 64, and status display 62, is controlled by a combination of software programs executed on system controller 500. User inputs typically include some combination of typing keyboards, computer pointing devices, buttons, rocker switches, joysticks, rotary dials, or touch screens. The system controller 500 manages the graphical user interface (GUI) presented on one or more of the displays (e.g. on image display 88). System controller 500 may receive inputs from buttons or other external user interface controls on the scope itself (or software controls through the GUI) to receive inputs for controlling aspects of the system.

Image processing circuitry 30 is one of three programmable logic devices, processors, or controllers in this embodiment, in addition to a system controller 500 and the exposure controller 40. Image processing circuitry 30, controller 500, exposure controller 40, system and program memories 56 and 54, video encoder 800 and display controller 82 may be housed within camera control module (CCM) 700, which is one example of a device control module 70 as described above.

CCM 700 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A medical device control module, either integrated with a medical device or configured to connect to a medical device, that is operable within at least two modes, the module comprising:
    at least one digital processor and associated RAM memory;
    tangible non-transitory computer readable media containing:
      (a) at least one binary image of a controlled type, for which updates are controlled by an external authority, for operating as a device within a first regulatory class;
      (b) at least one binary image of a non-controlled type for operating as a device within a second regulatory class;
      (c) boot manager program code executable by the digital processor to
        receive an indicator for performing at least one medical procedure that utilizes a medical device;
        based on the indicator, select one of the binary images for booting the medical device control module;
        determine if the selected binary image is a controlled type image, and if so, perform a verification of the image and then boot the medical device control module from the controlled type binary image;
    the at least one digital processor operable to, after booting from the controlled type binary image, execute program code from the controlled type binary image for operating the medical device control module, and controlling the medical device, as a first regulatory class medical device for performing the at least one medical procedure; and
    wherein the program code further comprises controlled-update program code executable by the at least one digital processor to verify a replacement controlled binary image, remove a selected controlled binary image, and replace it with the replacement controlled binary image and subsequently to recognize that a different medical device has been coupled to a medical device control module, obtain a device identifier for the different medical device, and based on the device identifier, select the replacement binary image and then boot the medical device control module from the replacement binary image.

2. The medical device control module of claim 1, which the boot manager program code further includes program code executable by the at least one digital processor for (i) recognizing that a medical device has been coupled to a medical device control module; (ii) obtaining a device identifier for the medical device; and (iii) wherein selecting one of multiple binary images is further based on the peripheral device identifier.

3. The medical device control module of claim 1, in which the medical device is a front end module for coupling an imaging scope to the medical device control module.

4. The medical device control module of claim 1, in which the boot manager program code further comprises code executable by the at least one digital processor for recognizing that a peripheral device has been coupled to the medical device control module and obtaining a device identifier for the peripheral device, wherein selecting one of multiple binary images is further based on the peripheral device identifier.

5. The medical device control module of claim 4, in which the peripheral device is a display module.

6. The medical device control module of claim 1, in which the medical device is a fluorescence imaging scope or a combination of a fluorescence imaging scope and a front end module for coupling the fluorescence imaging scope to the medical device control module.

7. The medical device control module of claim 1, in which the at least one binary image includes program code for a microprocessor and FPGA configuration code for configuring at least one FPGA in the medical device control module.

8. The medical device control module of claim 1, in which the program code further comprises update program code executable by the at least one digital processor to update a selected non-controlled binary image, and subsequently to recognize that a different medical device has been coupled to a medical device control module, obtain a device identifier for the different medical device, and based on the device identifier, select the replacement binary image and then boot the medical device control module from the updated binary image.

* * * * *